United States Patent [19]
Hill, III et al.

[11] Patent Number: 5,919,161
[45] Date of Patent: Jul. 6, 1999

[54] GUIDEWIRE MIGRATION CONTROLLER

[75] Inventors: E. Richard Hill, III, Berkeley; Glenn Davis, Sunnyvale; Brian Farley, Los Altos, all of Calif.

[73] Assignee: Devices for Vascular Intervention, Santa Clara, Calif.

[21] Appl. No.: 08/531,145

[22] Filed: Sep. 18, 1995

Related U.S. Application Data

[63] Continuation-in-part of application No. 08/237,690, May 4, 1994, Pat. No. 5,499,632.

[51] Int. Cl.$^6$ .................................................. A61M 37/00
[52] U.S. Cl. .............................................................. 604/95
[58] Field of Search .................................... 606/159, 167, 606/168, 169, 172, 180, 184, 185; 128/772; 604/95

[56] References Cited

U.S. PATENT DOCUMENTS

| | | |
|---|---|---|
| Re. 33,569 | 4/1991 | Gifford, III . |
| 4,732,163 | 3/1988 | Bonello et al. . |
| 4,771,774 | 9/1988 | Simpson . |
| 4,781,186 | 11/1988 | Simpson et al. . |
| 4,794,931 | 1/1989 | Yock . |
| 4,798,598 | 1/1989 | Bonello et al. . |
| 4,979,951 | 12/1990 | Simpson . |
| 4,986,807 | 1/1991 | Farr . |
| 5,000,185 | 3/1991 | Yock . |
| 5,007,917 | 4/1991 | Evans . |
| 5,041,089 | 8/1991 | Mueller et al. . |
| 5,071,425 | 12/1991 | Gifford, III . |
| 5,078,722 | 1/1992 | Stevens ................................ 604/22 |
| 5,084,010 | 1/1992 | Plain . |
| 5,085,662 | 2/1992 | Willard . |
| 5,087,265 | 2/1992 | Summers . |
| 5,092,873 | 3/1992 | Simpson et al. . |
| 5,100,424 | 3/1992 | Jung . |
| 5,108,411 | 4/1992 | McKenzie . |
| 5,135,531 | 8/1992 | Shiber . |
| 5,156,610 | 10/1992 | Reger . |
| 5,158,564 | 10/1992 | Schnepp-Pesch . |
| 5,226,909 | 7/1993 | Evans . |
| 5,250,059 | 10/1993 | Andreas . |
| 5,312,338 | 5/1994 | Nelson et al. ............................. 604/95 |
| 5,499,632 | 3/1996 | Hill, III et al. . |

*Primary Examiner*—John D. Yasko
*Attorney, Agent, or Firm*—Peninsula IP Group; Douglas A. Chaikin

[57] ABSTRACT

Disclosed herein is a guidewire migration controller for use with catheter devices such as atherectomy catheters. The guidewire migration controller includes a housing, a gripper insertable in the housing and a locking member. The locking member holds the gripper within the housing. The gripper has an opening for receiving a guidewire. The gripper permits the guidewire to rotate and holds the guidewire to control guidewire migration.

8 Claims, 3 Drawing Sheets

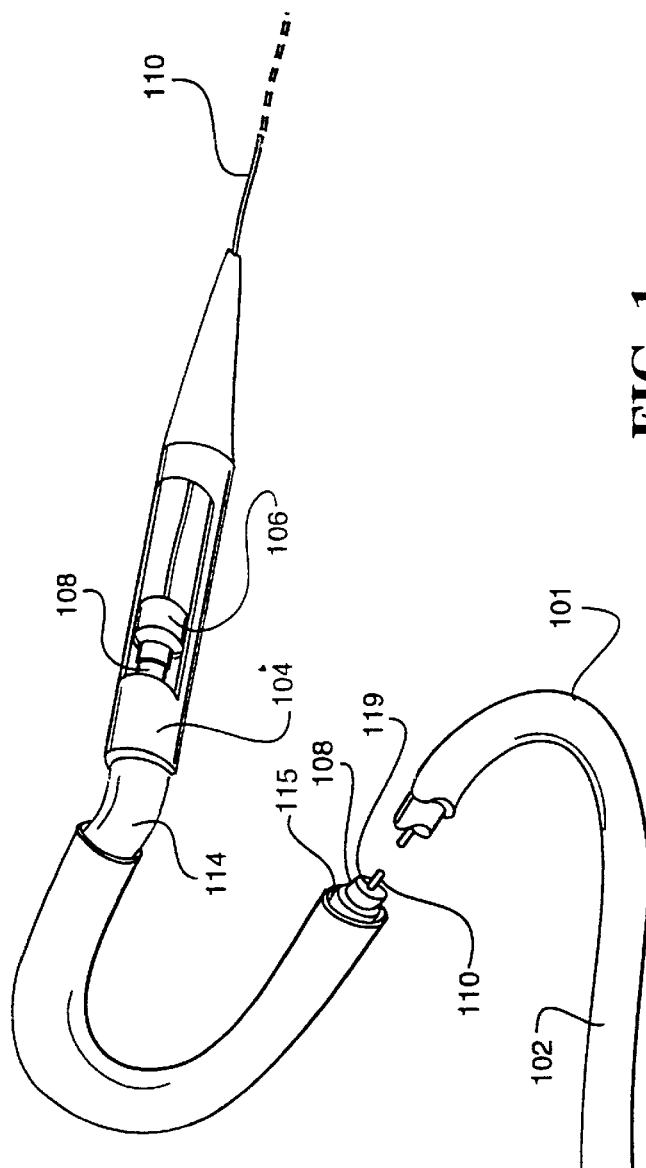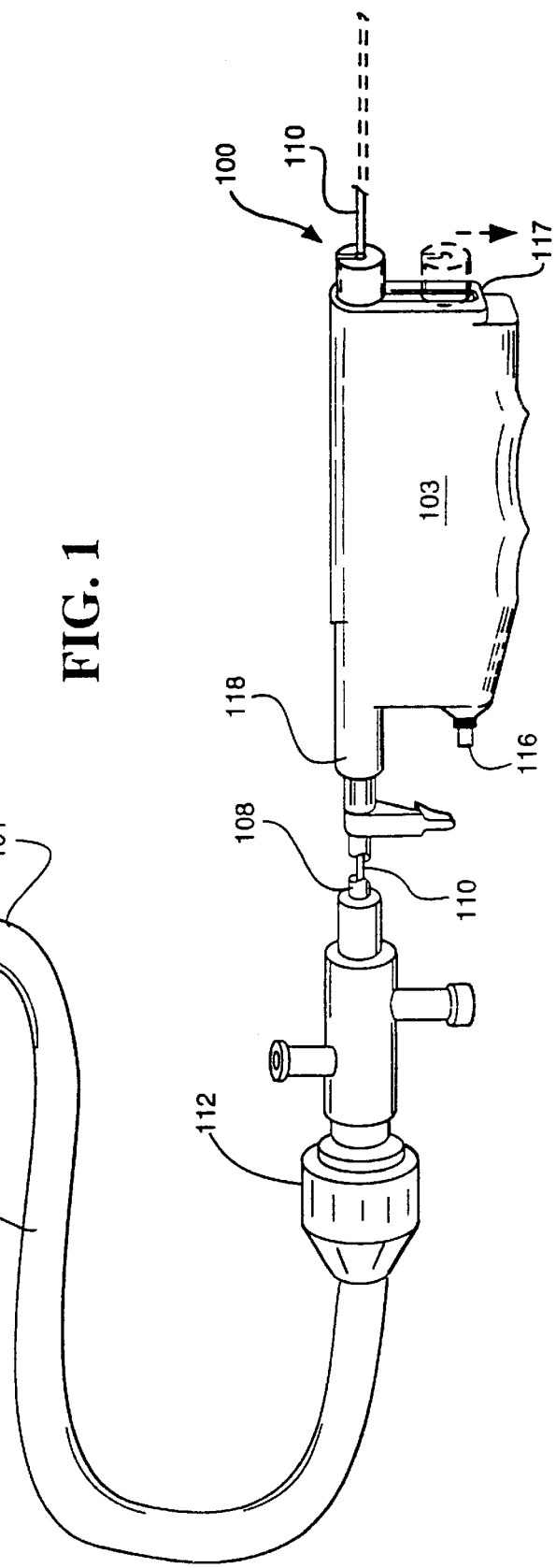
FIG. 1

GUIDEWIRE MIGRATION CONTROLLER

CROSS-REFERENCE TO RELATED APPLICATION

This patent application is a continuation-in-part of U.S. patent application Ser. U.S. Pat. No. 08/237,690, filed May 4, 1994 now U.S. Pat. No. 5,499,632.

BACKGROUND OF THE INVENTION

1. Field of Invention

This invention relates to catheter devices which rely on guidewires to direct the catheter to a desired location within a body. More particularly, this invention relates to guidewire controllers.

2. Previous Art

As described in U.S. Pat. Nos. 5,250,059; 5,084,010 and 4,479,952 which are specifically incorporated herein by reference, there exists a plethora of different catheter designs. Where directional atherectomy catheters are used, it is desirable to employ a guidewire to guide the catheter to the desired position within a body.

Typically, the catheter has a drive unit attached to a torque cable for rotating (or rotationally oscillating) a work element. The torque cable (cable) has a hollow interior. One end of the cable connects to the drive unit and the other end connects to the work element. Work elements include, for example, cutting devices, ablation elements and telemetry devices.

A guidewire slides within the hollow interior of the torque cable in order to guide the catheter into a desired location within the body. The guidewire, for example, can guide an atherectomy catheter to an occluded region in the vasculature of a human body.

The guidewire is manipulated to the desired location by rotating and feeding the guidewire from the drive unit through the torque cable. This feeding may be accomplished by hand, or otherwise.

The drive unit rotates the torque cable. A drive unit is disclosed in U.S. Pat. No. 4,771,774 which is incorporated herein by reference. A torque cable is disclosed in commonly assigned U.S. patent application Ser. No. 08/606,678 filed Feb. 2, 1996, Attorney Docket No. DEVI1434CON, the file wrapper continuation of U.S. patent application Ser. No. 08/165,058 filed Dec. 9, 1993, which is incorporated herein by reference. Rotation of the torque cable causes sympathetic rotation of the guidewire. Sympathetic rotation is the result of frictional forces developed between the rotating interior of the torque cable and the surface of the guidewire.

The torque cable can also be translated along the longitudinal axis of catheter independently of cutter rotation. Torque cable translation causes sympathetic translation of the guidewire, also known as migration. Migration of the guidewire during operation of the work element is undesirable because the guidewire may interfere with operation of the catheter and the work element. What is desired is a way of controlling the axial migration of the guidewire.

The guidewire must be able to rotate as the sympathetic action between the torque cable and guidewire may varyingly dictate. If the guidewire is kept from rotating at the proximal end, the spinning action of the torque cable against the guidewire may cause one end of the guidewire to twist and wind up with respect to the other end. This can cause the guidewire to deform and fail.

What is needed is a device for controlling guidewire migration along the torque cable. The device should allow the guidewire to spin during rotation and longitudinal motion of the torque cable. The device for controlling the guidewire migration should be adapted for use with various guidewire types, torque cables and drive systems.

SUMMARY OF THE INVENTION

It is a general object of this invention to provide a guidewire migration controller which prevents substantial migration of the guidewire through a torque cable during catheter operation.

It is another object of this invention to provide a device for controlling migration of a guidewire which adapts easily with a conventional drive unit.

It is another object of this invention to provide a guidewire migration controller which inhibits substantial migration of the guidewire without interfering with rotation of the torque cable.

In accordance with the above objects and those that will become apparent below, a device for controlling guidewire migration comprises:

a housing;
a guidewire gripper having an opening for gripping the guidewire, the guidewire gripper being insertable within the housing; and
a locking member for locking the guidewire gripper within the housing,
whereby, when the locking member locks the guidewire gripper within the housing, the guidewire gripper holds the guidewire to control guidewire migration.

In a preferred embodiment of the present invention the locking member and the housing each define an opening for receiving a guidewire.

In another preferred embodiment, the locking member rotatably attaches to the housing.

In another preferred embodiment, the gripper rotates with the locking member.

In another preferred embodiment, the locking member has a rotation adjuster for aligning the openings in the gripper and the locking member with the opening in the housing.

In another preferred embodiment, the housing slidably attaches with a drive unit of an atherectomy catheter. The housing normally occupies a first position with respect to the drive unit to hold a guidewire. The housing slides to a second position to release the guidewire.

In another preferred embodiment, the housing includes a body which defines an inner race. The locking member includes an annulus. The inner race rotatably connects with the annulus.

It is an advantage of the present invention to provide a guidewire migration controller which controls migration of a guidewire through a torque cable of a catheter.

It is another advantage of the present invention to provide a device for controlling guidewire migration which can be adapted for use with a conventional drive unit.

It is another advantage of the present invention to provide a guidewire migration controller which does not significantly interfere with rotation of the torque cable.

BRIEF DESCRIPTION OF THE DRAWINGS

For a further understanding of the objects and advantages of the present invention, reference should be had to the following detailed description, taken in conjunction with the accompanying drawing, in which like parts are given like reference numerals and wherein:

FIG. 1 illustrates, in perspective view, the guidewire migration controller in accordance with this invention in connection with a typical catheter.

DETAILED DESCRIPTION OF THE INVENTION

Figure 2:
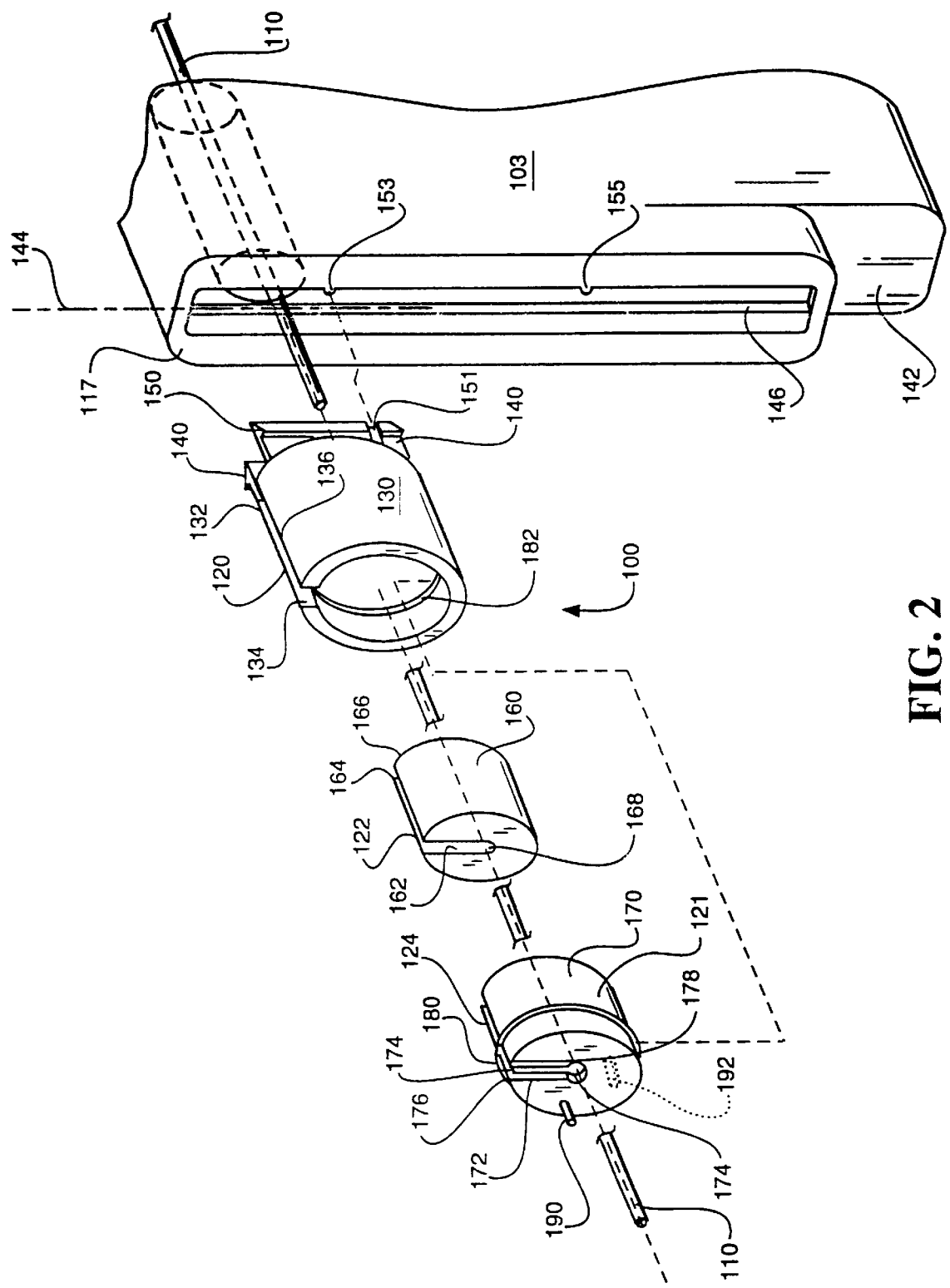
FIG. 2 is an exploded view of the guidewire migration controller of FIG. 1.

The invention will now be described with specific reference to FIG. 1 which illustrates the guidewire controller generally designated by the reference numeral 100. The guidewire controller 100 is shown in operable attachment with an atherectomy catheter 101.

The atherectomy catheter 101 has a drive unit 103, a catheter body 102, a work element housing 104, a work element 106, a torque cable 108, and a guidewire 110. The catheter body 102 has a proximal end 112, a distal end 114 and a catheter lumen 115 extending therebetween. The torque cable 108 extends through the catheter body 102 through the catheter lumen 115, between the proximal end 112 and the distal end 114. The work element housing 104 attaches to the distal end 114 of the catheter body 102. The work element 106 attaches to the torque cable 108. The work element housing 104 houses the work element 106.

The drive unit 103 has a proximal end 117 and a distal end 118. The distal end 118 of the drive unit 103 connects with the proximal end 112 of the catheter body 102. The guidewire controller 100 attaches to the proximal end 117 of the drive unit 103. The torque cable 108 attaches within the drive unit 103. The drive unit 103 rotates the torque cable 108 and thereby actuates the work element 106.

The torque cable 108 is a hollow tube having a central lumen 119 through which the guidewire 110 is fed. Rotation of the torque cable 108 may cause sympathetic rotation of the guidewire 110 within the torque cable 108.

The guidewire 110 facilitates positioning of the atherectomy catheter 101 (e.g. to within the coronary artery). Preferably, the work element 106 is a cutter which rotates (or rotationally oscillates) to remove tissue invaginated by the work element housing 104 (e.g. atheroma). An example of a catheter device and the use thereof is described in U.S. Pat. No. 5,312,425 which is incorporated herein by reference.

The guidewire 110 is made from material such as spring steel or Nitinol. The guidewire 110 has a diameter of between 0.009" and 0.018".

A switch 116 is provided with the drive unit 103 to actuate the drive unit 103. The drive unit has an electronically powered motor. Accordingly, the drive unit 103 includes a power source e.g. batteries, or an A/C plug. The switch 116 toggles the operation of the drive unit 103 in an on/off condition. It can be appreciated that various switches 116 can be employed which selectively regulate the rotational speed of the torque cable 108. An example of a drive unit which can be adapted for use with the present invention is disclosed in U.S. Pat. No. 4,771,774 which is incorporated herein by reference.

With particular reference to FIG. 2, the guidewire migration controller 100 is shown in an exploded perspective view. The guidewire migration controller 100 includes a housing 120, a gripper 122 and a locking member 124. The guidewire 110 passes through the drive unit 103 and the guidewire migration controller 100. The gripper 122 permits rotation of the guidewire 110 and holds the guidewire 110 to selectively prevent guidewire migration.

The housing 120 has a body 130 which is resilient. The body 130 has edges 134 and 136 which define an opening 132 therebetween. The opening 132 extends longitudinally along the body 130 for receiving the guidewire 110. The edges 134 and 136 normally remain separated from each other by the opening 132.

The housing 120 includes a pair of ears 140 which extend from the body 130. Each ear 140 has a rail member 150. The drive unit 103 presses the ears 140 together when the housing 120 connects with the drive unit 103. When the ears 140 are pressed together the housing 120 flexes and the ends 134 and 136 move toward each other to hold the gripper 122 and the locking member 124 within the housing 120.

The drive unit 103 has a proximal end 142. The proximal end 142 has a track member 146 which defines a track axis 144. The ears 140 slidably connect with the track member 146. The rail members 150 lock the ears 140 with the track member 146. The track member 146 contacts the ears 140 to press the edges 134 and 136 together and slidably hold the housing 120 with the drive unit 103.

The gripper 122 has a gripper body 160 with a center slot 168 and edges 164 and 166. The edges 164, 166 and the center slot 168 define an opening 162 therebetween. The gripper body 160 is resilient and compressible so that the ends 164 and 166 are adjustably spaced apart to receive the guidewire 110. Preferably, the opening is normally between several thousandths of an inch to one hundredth of an inch thick. The opening 162 is reduced in thickness when the gripper body 160 is compressed by the housing 120.

The gripper 122 is made from a resilient material suitable for gripping a thin metal wire. The resilient material is preferably polymeric, such as for example, a polyurethane, RTV silicone, silicone rubber and varied elastomeric materials. It will be appreciated that when the gripper is inserted within the housing 120 and held by the locking member 124, the ends 164 and 166 are moved together, the gripper 122 (including the center slot 168) grips the guidewire 110.

The locking member 124 has a body 170. The body 170 has edges 176 and 178. The edges 176 and 178 define a portion of an opening 172 therebetween. The body 170 defines a center opening 174. The edges 176 and 178 oppose each other and are normally apart. The opening 172 and the center opening 174 receive the guidewire 110.

The body 170 of the locking member 124 has an annulus 180 which circumscribes a portion of the body 170. The housing body 130 includes an inner race 182. The inner race 182 is annular in shape and configured for receiving the annulus 180 of the locking member. The inner race 182 and the annulus 180 rotatably connect.

Although an annulus 180 and an inner race 182 are shown, alternate rotatable connections can be employed in accordance with the present invention. For example, a bearing structure can be added to rotatably attach the locking member 124 the housing 120. Alternatively, the locking member 124 can have an inner race and the housing 120 can have an annulus to provide a rotatable connection therebetween.

When the guidewire gripper 122 grips the guidewire 110 and the locking member 124 locks with the housing 120, and the guidewire 110 sympathetically rotates with the torque cable 108 (FIG. 1), the locking member 124 and the guidewire gripper 122 rotate with the guidewire 110.

The drive unit 103 includes protuberances 153 and 155 attached to the track member 146. The rail member 140 of the housing 130 defines a portion of a detent 151. The ear 150 of the rail member 140 defines a portion of the detent 151. The detent 151 cooperates with the protuberance 153 to lock the housing 120 in a first position with the motor drive unit (FIG. 1). The housing 120 slides within the track member 146. The detent 151 cooperates with the protuberance 155 to lock the housing 120 in a second position (shown in phantom in FIG. 3). When the housing 120 attaches to the drive unit 103, the track member 146 urges the rail members 140 together to compress the housing 120. The housing is resilient and holds the rail members 140 against the track member 146 to hold the housing 120 and the drive unit 103 together.

The locking member 124 is provided with a rotation adjuster 190. The rotation adjuster 190 aligns the openings 162 and 172 of the gripper 122 and locking member 124, respectively, with the opening 132 of the housing 120. The rotation adjuster 190 is an extended pin grip. In an alternate embodiment (shown in phantom) the rotation adjuster 190 includes a recess 192.

Figure 3:
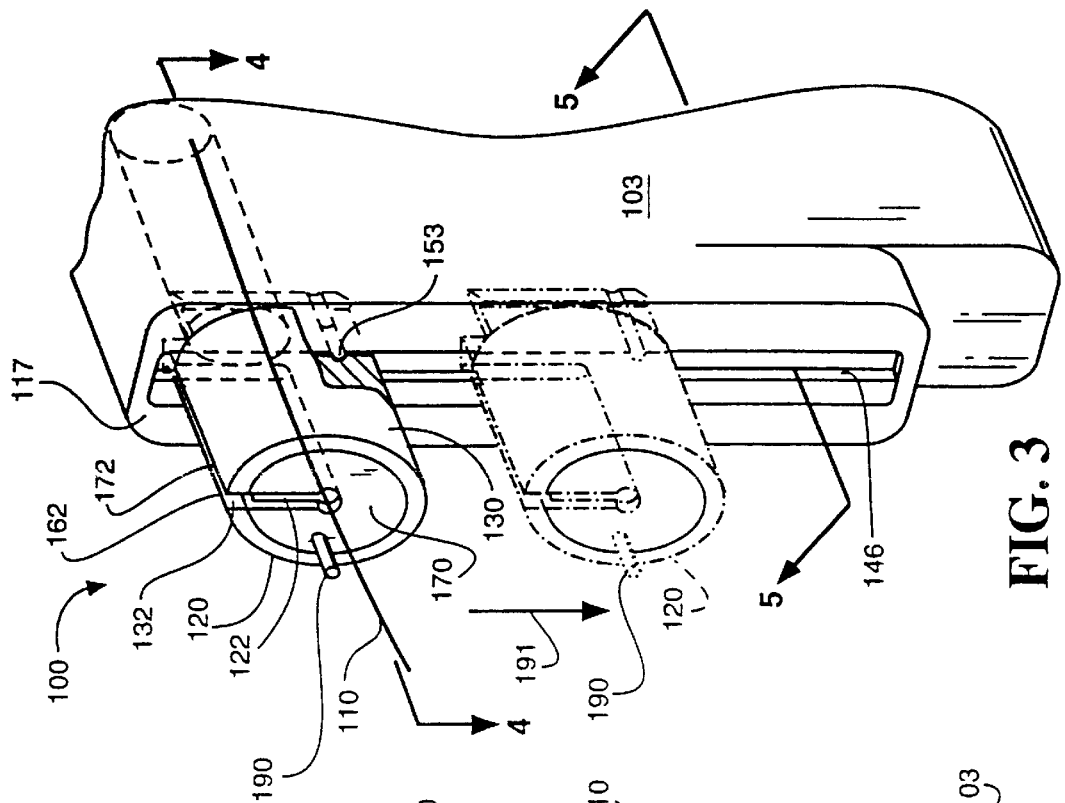
FIG. 3 is a perspective view of the guidewire migration controller of FIG. 2.

With particular reference to FIG. 3 the guidewire 110 extends through the drive unit 103 and the guidewire migration controller 100. The housing 120 of the guidewire migration controller 100 is in the first position with respect to the drive unit 103 to receive the guidewire 110. The housing 120 slides along the track member 146 in the direction of the arrow 191 and moves to the second position, generally shown in phantom (see also FIG. 1). In the second position, the guidewire migration controller 100 releases the guidewire 110.

The openings 132, 162 and 172 of the housing 120, the gripper 122 and the locking member 124 respectively align for reciprocally receiving and releasing the guidewire 110.

The locking member 124 holds the gripper 122 so that the opening 162 of the gripper maintains alignment with the opening 172 of the locking member 124. The rotation adjuster 190 adjusts the alignment of the openings 172 and 162 in the locking member 124 and the gripper 122 respectively to align the openings 172 and 162. With the openings 172, 162, and 132 aligned, the housing is moveable between the first and second positions to reciprocally receive and release the guidewire 110.

Figure 4:
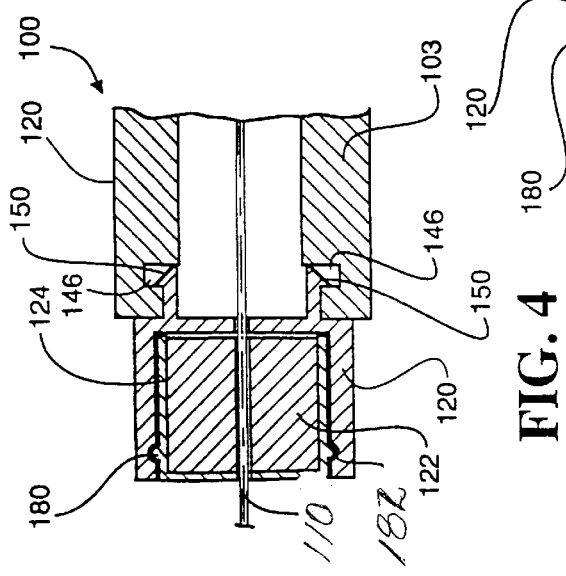
FIG. 4 is a cross-sectional view of the guidewire migration controller of FIG. 3 as seen along line 4—4 in the direction of the arrows.

With particular reference to FIG. 4, the guidewire migration controller 100 is shown connected with the drive unit 103. The rail members 150 attach within the track member 146 of the drive unit 103. The gripper 122 holds the guidewire 110.

It can be appreciated that when the guidewire 100 rotates sympathetically in response to rotation of the torque cable 108 (FIG. 1), the guidewire 110 rotates the gripper 122. The gripper 122 and the locking member 124 rotate together. The annulus 180 of the locking member 124 rotates within the race 182 of the housing 120.

Figure 5:
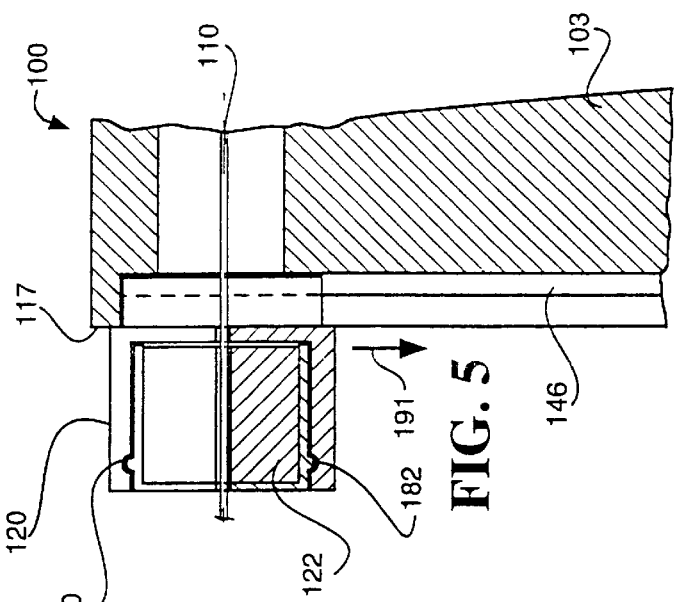
FIG. 5 is a cross-sectional view of the guidewire migration controller of FIG. 3 taken along line 5—5 in the direction of the arrows.

With particular reference to FIG. 5, the guidewire migration controller 100 is shown attached to the track member 146 of the drive unit 103. The housing 120 occupies the first position as shown in FIG. 3. In the first position, the guidewire migration controller 100 holds the guidewire 110 to control guidewire migration. The housing 120 is reciprocally slideable along the track member 146 in the direction of the arrow 190 to reciprocally receive and release the guidewire 110.

While the foregoing detailed description has described the guidewire migration controller in terms of a preferred embodiment, it is to be understood that the above description is illustrative only and not limiting of the disclosed invention. Particularly, the shape of the gripper can vary to accommodate various types of guidewires. Additionally, the housing can be adapted for use with a variety of catheter devices. This invention is to be limited only by the claims as set forth below.

What is claimed is:

1. A device for controlling migration of a guidewire, comprising:

a housing including a body which defines an inner race;

a guidewire gripper rotatably attached within the housing for holding the guidewire; and a locking member for holding the guidewire gripper within the housing, the locking member including an annulus, the inner race and the annulus being rotatably connectable, whereby when locking member holds the guidewire gripper within the housing, the guidewire gripper can grip the guidewire to control guidewire migration while allowing the guidewire to rotate.

2. A device as set forth in claim 1, wherein the locking member is rotatably attachable with the housing, the locking member locks the guidewire gripper about the guidewire, the guidewire gripper and the locking member rotate together with respect to the housing.

3. A device for controlling migration of a guidewire, comprising:

a housing;

a guidewire gripper rotatably attached within the housing for holding the guidewire, the guidewire gripper defining an opening for receiving the guidewire; and a locking member for holding the guidewire gripper within the housing, the locking member having two edges defining a opening therebetween, the guidewire extending through the opening, whereby when locking member holds the guidewire gripper within the housing, the guidewire gripper can grip the guidewire to control guidewire migration.

4. A device as set forth in claim 3, wherein the locking member is fabricated from resilient material, the two edges being moveable with respect to each other.

5. A device for controlling migration of a guidewire, comprising:

an atherectomy catheter including a catheter body, a torque cable and a drive unit, the torque cable having a cable lumen for receiving a guidewire, the torque cable being rotatable and extending through the catheter body, the drive unit being attached to the torque cable for rotating the torque cable;

a housing attached to the drive unit, the housing having a set of projecting ears, the drive unit having a track member, the projecting ears slidably attaching to the track member;

a guidewire gripper being insertable within the housing, the guidewire gripper having an opening for receiving the guidewire; and a locking member for locking the guidewire gripper within the housing, whereby when the drive unit rotates the torque cable and the locking member locks the guidewire gripper within the housing, the guidewire gripper grips the guidewire to control guidewire migration.

6. A device as set forth in claim 5, wherein the housing normally occupies a first position with respect to the track member, the housing slides along the track member to a second position, in the first position the guidewire gripper holds the guidewire to prevent axial translation of the guidewire with respect to the catheter, in the second position the guidewire releases the guidewire.

7. A device as set forth in claim 6, further comprising a means for securing the housing with the drive unit in the first position and in the second position.

8. A device for controlling migration of a guidewire, comprising:

an atherectomy catheter including a catheter body, a torque cable and a drive unit, the torque cable having a cable lumen for receiving a guidewire, the torque cable being rotatable and extending through the catheter body, the drive unit being attached to the torque cable for rotating the torque cable;

a housing attached to the drive unit the housing having a body with an inner race;

a guidewire gripper being insertable within the housing; and a locking member for locking the guidewire gripper within the housing, the locking member having an annulus, the inner race and the annulus rotatably connecting, the locking member and the gripper rotating when the drive unit rotates the torque cable and the torque cable sympathetically rotates the guidewire, whereby when the drive unit rotates the torque cable and the locking member locks the guidewire gripper within the housing, the guidewire gripper grips the guidewire to control guidewire migration.

* * * * *